United States Patent
Heraud

(10) Patent No.: US 7,901,210 B2
(45) Date of Patent: Mar. 8, 2011

(54) ROTATABLE FILE DENTAL TREATING DEVICE

(75) Inventor: Roger Heraud, Avensan (FR)

(73) Assignee: Xelyx, Blanquefort (FR)

( * ) Notice: Subject to any disclaimer, the term of this patent is extended or adjusted under 35 U.S.C. 154(b) by 745 days.

(21) Appl. No.: 11/665,990

(22) PCT Filed: Oct. 20, 2005

(86) PCT No.: PCT/FR2005/050877
§ 371 (c)(1), (2), (4) Date: Dec. 21, 2007

(87) PCT Pub. No.: WO2006/045974
PCT Pub. Date: May 4, 2006

(65) Prior Publication Data
US 2008/0090203 A1 Apr. 17, 2008

(30) Foreign Application Priority Data
Oct. 25, 2004 (FR) .................................... 04 52430

(51) Int. Cl.
A61C 5/02 (2006.01)

(52) U.S. Cl. .............................. 433/224; 433/98; 433/27

(58) Field of Classification Search .................... 433/27, 433/72, 75, 77, 98, 102, 106, 114, 224; 600/587, 600/590
See application file for complete search history.

(56) References Cited

U.S. PATENT DOCUMENTS

| 4,193,408 A | 3/1980 | Fujino |
| 5,902,105 A | 5/1999 | Uejima et al. |
| 5,980,248 A | 11/1999 | Kusakabe et al. |

Primary Examiner — Cris L Rodriguez
Assistant Examiner — Eric Rosen
(74) Attorney, Agent, or Firm — Young & Thompson

(57) ABSTRACT

A rotatable file dental treating device (1) driven by a motor (2) includes elements (3, 18) for determining a root-canal position instruction related to a tooth apex, elements (4) for stopping the motor according the file (1) position with respect to the position instruction and first members (5, 6) for measuring and calculating the canal length (L) remaining between the file and the position instruction. The device includes second members (7, 7a, 7b) for calculating a value (D) derived from the remaining canal length and third members (8, 8a, 8b, 8c, 8d, 8e) for combining the derived value and the remaining canal length and the combination of the derived value. The canal length produced by the calculating elements (6, 7, 8, 8a, 8b, 8c, 8d, 8e) controls the motor turn-off in such a way that the rotation of the file is stopped in anticipation of the position instruction.

15 Claims, 4 Drawing Sheets

ROTATABLE FILE DENTAL TREATING DEVICE

CROSS-REFERENCE TO RELATED APPLICATIONS

The present Application claims priority to and incorporates by reference PCT/FR2005/050877 filed Oct. 20, 2005 and French Application No. 0452430 filed Oct. 25, 2004.

STATEMENT REGARDING FEDERALLY SPONSORED RESEARCH OR DEVELOPMENT

None.

THE NAMES OF THE PARTIES TO A JOINT RESEARCH AGREEMENT

None.

INCORPORATION-BY-REFERENCE OF MATERIAL SUBMITTED ON A COMPACT DISC

None.

BACKGROUND OF THE INVENTION (1) Field of the Invention

This invention relates to the rotary-file dental treatment devices.

(2). Description of Related Art

Currently, the dental treatment devices that use rotary files, such as the nickel-titanium files of different diameters based on the dental work to be done, in root canals have means for measuring torque and/or means for measuring root canal length to limit the breaking of files and/or to stop the rotation of the file in the apical region, but have few if any safety means for avoiding the breaking of files, for monitoring the precision of the stopping of the file in the apical region or else for keeping dental debris from being projected into or under the apical region.

For reasons of stability of measuring or design, regardless of the measuring means, the measuring of the root canal position of the file is an averaged and smoothed measurement that makes it possible to eliminate outliers or speed fluctuations of the file.

Such a smoothed measurement does not at any moment provide the exact position of the file, whereby a sometimes significant delay is noted on the measurement of position of the file.

This is all the more significant provided that the practitioner is to apply a back-and-forth movement to bring out the dental sludge and provided that the speed of insertion of the files in the tooth is not controlled.

This situation brings about a non-negligible source of error on the depth reached by the file in the canal with regard to a precise setting of the depth to be reached.

The documents U.S. Pat. No. 5,902,105 and U.S. Pat. No. 5,980,248 describe dental treatment devices that comprise means that are suitable for gradually slowing the speed of rotation of a motor driving the file before the stopping thereof so that the work of the file decreases with the lowering of the speed of rotation of the motor.

One drawback of this method is that when the motor slows down, the file no longer works normally and in particular can be caused to work by torsion impacts, which fatigues the file and reduces its reliability.

In addition, when the file is in the apical region, a slowing of the file can cause a screwing of the file into the tooth, which carries with it the risk of piercing the conduit, with debris being projected under the apex, source of infection, or breaking the file.

A known process for stopping the motor consists in measuring the current drawn by the motor at the terminals of a resistor inserted into the power circuit, amplifying and integrating this signal, then converting it by means of an analog/digital converter so as to compare the result of the conversion to a value that represents a given torque limit before acting on the control integrator and electrically stopping the motor in its motion.

According to this process, the motor will stop only when the torque that is braking has overcome the inertia of the kinematic and logical unit.

This process has the additional drawback that the delays that are introduced by the measuring chain repel the desired stopping action by a non-negligible period of time that can produce the fracturing or the breaking of the file in the tooth.

To avoid the screwing of the file, it was also provided in the document U.S. Pat. No. 5,980,248 to rotate the file backwards at high speed after the apical stop. Such a device has the drawback of sending dental debris back into the apex, which is a source of contamination of the dental cavity.

For its part, the document EP 0 966 237 describes a process and a device for measuring in real time the distance between the distal end of an electrode that is inserted in the radicular canal of a tooth and the apex of said canal and the location of the apex of a tooth.

BRIEF SUMMARY OF THE INVENTION

This invention relates to a dental treatment device with an improved rotary file in that it comprises a device that makes it possible to anticipate the stopping of the motor relative to a position setting that is defined relative to the depth of the canal, making it possible to avoid piercing the apex of the tooth, to prevent the return of debris toward the apex of the tooth and minimizing the fatigue of the file and the risks of breaking the latter in the tooth. According to an advantageous embodiment, the device comprises a control of the motor torque with a device for stopping upon exceeding a maximum torque.

This invention also relates to a process for controlling a rotary-file dental treatment device that allows a very quick stopping of the motor rotating the file and, in relation to the measuring of the root canal length, a precise stop in the apical region (between 0 and 2 mm of the apex).

More specifically, the invention relates primarily to a rotary-file dental treatment device that is driven by a motor that comprises means for fixing a root canal position setting relative to the apex of a tooth, means for stopping the motor based on the position of the file relative to said position setting, first means for measuring and calculating the remaining root canal length between the file and the position setting, characterized in that it comprises second means for calculating at least one value derived from the remaining root canal length and third means for calculation, suitable for combining the derived value and the remaining root canal length, whereby the combination of the derived value and the root canal length by the calculating means controls the means for controlling the stopping of the motor so as to stop the rotation of the file in anticipation of the position setting.

Thus, the device according to the invention makes it possible to anticipate the stopping of the motor based on the speed of insertion of the file in the canal.

According to the invention, said derived value can comprise in particular the first derivative of the remaining root canal length and/or the second derivative of the remaining root canal length.

Advantageously, the third calculating means comprise means for weighting the derived value by a calculated adjustment coefficient.

The device for anticipating the stopping of the motor according to the invention makes it possible to bring and to stop the end of the file exactly at the value of the setting, regardless of the speed of penetration of the file, without exceeding the apex (in particular in a wide canal or a non-formed apex) and makes it possible to compensate for the different measuring delays as well as the differences of the support forces on the device between practitioners.

The invention also relates to a dental treatment device that is characterized in that it comprises means for selecting a reference maximum motor torque, means for measuring the torque applied to the file, and means for calculating the exceeding of the maximum torque controlling the means for stopping in the rotation of the motor.

The invention also relates to a process for controlling rotation of a file of a dental treatment device that comprises primarily the repeated determination of a distance from the file to a root canal position setting relative to the apex of a tooth, the repeated determining of a value that is derived from said distance, and the repeated calculation of an early stopping position of the rotation of the file based on the distance from the file to said position setting weighted by a coefficient that is based on said derivative.

More particularly, the process comprises a stage for anticipation of the activation of means for stopping the file in rotation based on the value of said derivative.

BRIEF DESCRIPTION OF THE SEVERAL VIEWS OF THE DRAWINGS

Other characteristics and advantages of the invention will be better understood from reading the following description of a nonlimiting embodiment of the invention with reference to the figures that show.

DETAILED DESCRIPTION OF THE INVENTION

Figure 1:
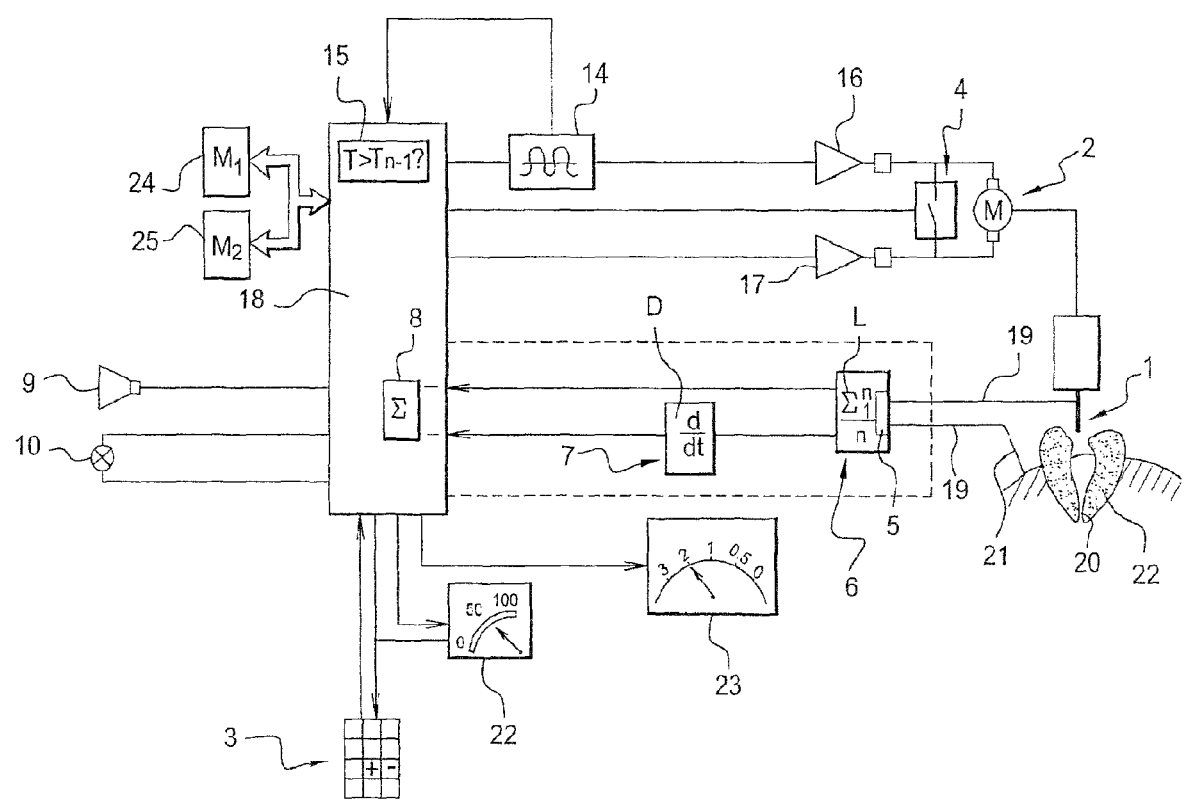
In FIG. 1: A diagrammatic representation of a device according to the invention.

The dental treatment device shown in FIG. 1 comprises a rotary file 1 that is driven by a motor 2.

The device comprises, according to the prior art that is described in the document EP 0 966 237, a system for measuring the distance from the file 1 to the apex 20 of a tooth 22. According to the example, this system is based on the use of the file as a first electrode and the use of a second electrode 21. The electrodes are connected by electric connections 19 to first measuring means 5 combined with first calculating means 6. The measuring means according to FIG. 1 comprise an analog part 5 and an analog-digital conversion part, whereby the calculating means 6 comprise means for summation of a series of measurements and averaging by division of the sum of measurements by the number of measurements, whereby this operation is carried out, for example, within a microprocessor 18.

Figure 3A:
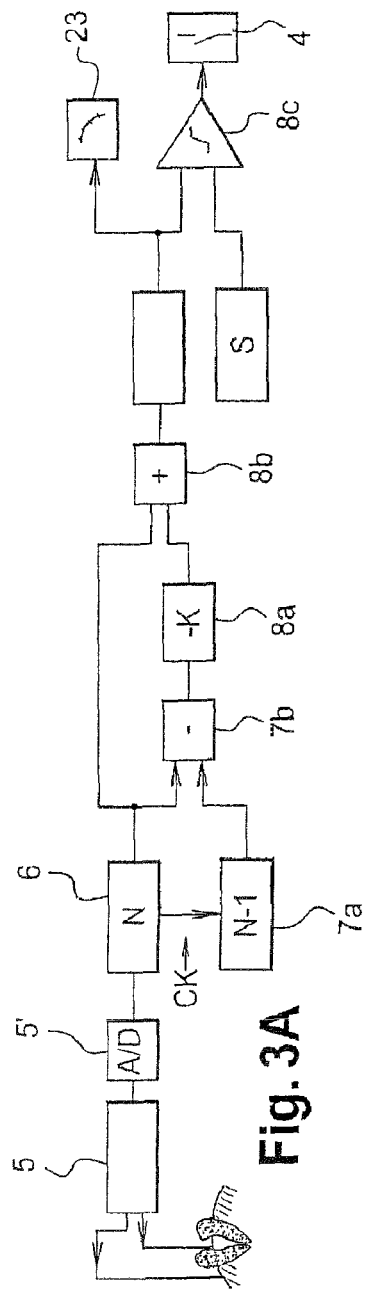
In FIGS. 3A, 3B, and 3C: Variant embodiments of constituent elements of the device according to the invention.

In the example of FIG. 3A, the analog-digital conversion part is shown under reference 5'.

The device comprises means 3, 18 for fixing a root canal position setting relative to the apex of a tooth. These means comprise a data input device, such as a keyboard 3, and the microprocessor 18. The selected setting can be displayed on a display device 23.

The setting corresponds to how far it is desired to keep the device from the apex of the tooth.

The device comprises means 16, 17 for control of the motor 2, whereby these means make it possible to rotate the file in forward or in reverse.

The stopping of the motor is controlled based on the position of the file 1 relative to the selected position setting.

As seen above, the device comprises first means for measuring 5 and calculating 6 the remaining root canal (L) length between the file and the position setting.

According to the invention, the device also comprises second calculating means 7 of at least one derived value (D) of the remaining root canal length.

In the embodiment of FIG. 3A, the calculating means 7 are broken down in a memory register of an N−1 measurement of the remaining distance and a subtractor element 7b that subtracts the value of an N-order measurement from the N−1-order measurement, which makes it possible to obtain the variation of distance and therefore an image of the derivative of the length at a given moment sequenced by a clock CK. The function diagrammed in FIG. 3 can advantageously be produced within the microprocessor 18 of FIG. 1.

The device that is diagrammed in FIG. 1 also comprises third calculating means 8, suitable for combining the derived value and the remaining root canal length, whereby the combination of the derived value and the root canal length by the calculating means 6, 7, and 8 control the means for stopping the motor so as to stop the rotation of the file in anticipation of the position setting.

Said derived value (D) comprises in particular the first derivative of the remaining root canal length.

This derived value is the derivative of the displacement of the file and corresponds to the progression speed of the file in the root canal during the insertion.

This speed is obtained by derivation of the measurement of the remaining root canal length at second calculating means 7; the third calculating means 8 comprise means for weighting the derived value (D) by an adjustment coefficient that is calculated so that the result of the calculation acts on the setting by addition, averaging an adjustment coefficient so that the stopping of the motor is carried out before the setting value is reached.

The third calculating means that are described in detail within the scope of the example of FIG. 3A comprise an operation 8a for multiplication of the value calculated by a weighting coefficient K at means 7b and an operation 8b for addition of the weighted derived value to the measured value.

As seen above, the calculating means 6, 7, and 8 can be produced by a microcontroller or microprocessor 18 and a program located in a permanent memory 24, whereby the measuring data and the calculated data are stored and treated in a dynamic memory 25.

To obtain the derivative, a pair of measurements of position separated by a given time, for example 50 milliseconds, is put into memory, and one is subtracted from the other, the difference then shows the deviation, whether more or less, whereby this operation is iterated according to a sequencing defined by the clock CK as the file works along.

According to the example, the positive value provided by the progress of the file toward the apex rather than a negative distance difference is the aspect of interest to us. The setting being positive, the absolute value of the derivative is calculated to obtain a positive value.

The coefficient K will be defined based on the parameters of the device and in particular delays in the measuring chain, the speed of rotation of the motor, and its capacities to stop brusquely to format the derivative before adding it to the setting so as to provide a position limit that is calculated at any moment to trigger the early stopping of the motor.

Thus, the invention makes it possible, despite the different delays such as the filtering of the measurement and other delays of the measuring chain, to bring and to stop the end of the file exactly at the setting value, regardless of the speed of penetration of the file, without exceeding the apex and in particular in a wide root canal or unformed apex.

Still according to FIG. 3A, the result that is obtained by the calculating means 8 is directed, on the one hand, toward display means 23 and compared, on the other hand, at a comparator 8c, to a reference threshold S corresponding to the limit that is not to be exceeded so as to guide the stopping means 4.

According to an alternate or complementary embodiment, said derived value (D) comprises the second derivative of the remaining root canal length, whereby this value is then representative of the acceleration, which is the double derivative of the displacement, instead of the speed, making it possible to stop the motor even more quickly in a screwing process, for example, or the acceleration of the file is strong.

Figure 3B:
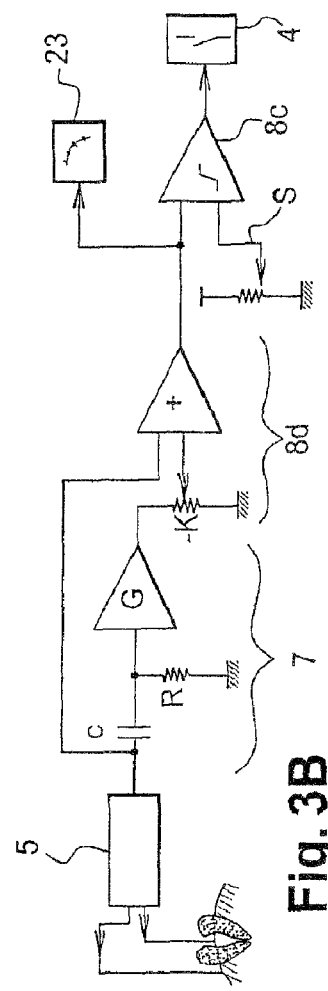
Figure 3C:
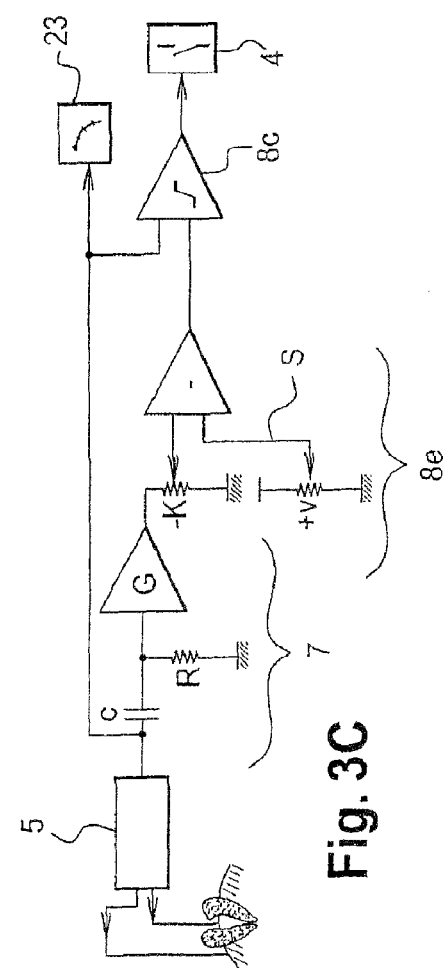

Other embodiments are shown in FIGS. 3B and 3C.

FIG. 3B relates to an embodiment for which the means for calculating the derivative are produced in the form of an analog differentiator; the calculating means 8d that are suitable for combining the measured value and the derivative consist of an analog summing integrator that adds a voltage that is representative of the derivative assigned by a weighting coefficient K.

According to this figure, the summed value is transmitted, on the one hand, with a display means 23, and, on the other hand, compared at a comparator 8c to a voltage that is representative of the threshold that is not to be exceeded, whereby the comparator controls the means 4 for stopping upon exceeding said voltage.

FIG. 3C shows a variant embodiment for which the measurement of distance by the measuring means 5 is, on the one hand, directly transmitted by display means 23, on the other hand transmitted to an analog differentiator stage that constitutes the calculating means 7 of the derivative, whereby the latter is weighted at calculating means 8e by a coefficient K and reduced by a coefficient that is representative of a threshold S and compared at a comparator 8c to the measured distance value to guide the stopping means.

Figure 2:
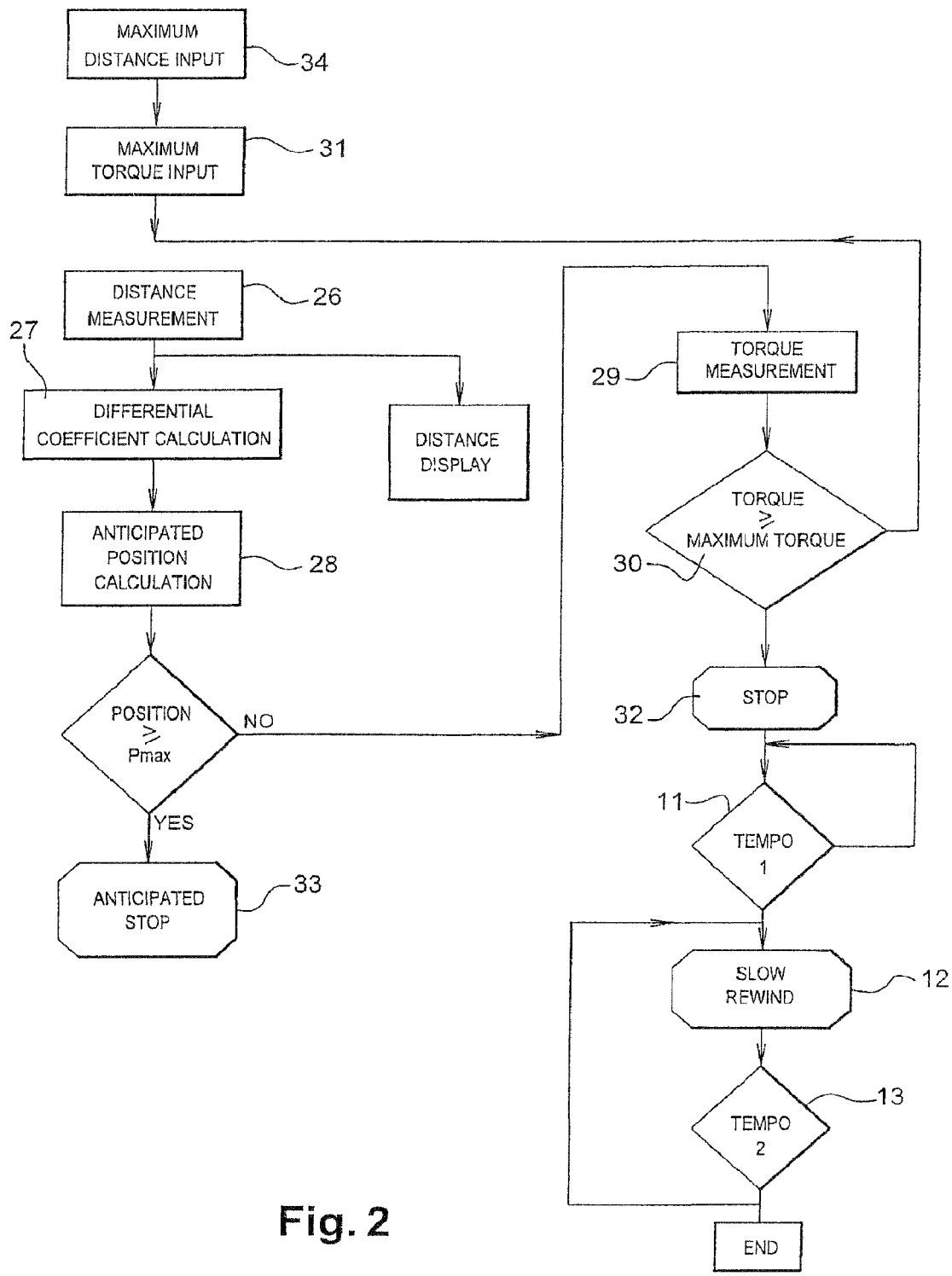
In FIG. 2: An example representing the stages of the process according to the invention.

The invention also relates to a process as described in FIG. 2 and comprising in particular the repeated determination g of a distance from the file to a root canal position setting relative to the apex of a tooth by a measurement 26, the repeated determination of a derived value of said distance by calculation 27 and the repeated calculation 28 of an early stopping position of the rotation of the file based on the distance from the file to said position setting weighted by a coefficient based on said derivative.

In the case of a device comprising a digital calculator such as a microprocessor 18, the repeated determination is a periodic determination or an intermittent succession of measurements.

In the case of an analog system, the repeated determination is continuous.

The process comprises a stage for anticipation of the activation of means for stopping in rotation the file based on the value of said derivative.

Another method that can be used to allow an early triggering of the motor is to subtract, after formatting, the derivative from the measurement.

This method can be used when the calculated measurement is a distance approaching a fixed setting in an insertion movement.

In addition to the implementation of the process, the device of FIG. 1 comprises additional means such as means for alerting an operator, auditory means 9 or visual means 10 triggered upon an activation of the stopping means or triggered as the distance to the setting decreases.

Within the framework of the use of a direct current motor fed by a device with pulse width modulation, the invention comprises, in an advantageous embodiment, a stopping device for detecting a torque exceeding a maximum value defined in advance and entered in the device with input means 3 as diagrammed in FIG. 1 in relation to a memory program of the torque value at a moment t and comparison of the torque value memorized with the memorized maximum torque value.

The motor, for example a rotor motor without iron and with low inertia, is controlled in speed at a preset speed either by design or by input through input means 3. A conventional speed for the rotation of the file is, for example, on the order of 300 rpm.

Regulation of the speed of the motor is obtained by control of the pulse width of the PWM (pulse width modulation) control device through a comparator between the FEM (electromotive force) applied to the motor and a setting that is representative of the speed of the motor.

The PWM generator is guided through a control comprising the measurement of the electromotive force at the level of the motor through a digital integrator and/or differentiator so that when the speed has a tendency to decrease because of a demand for torque, the pulse width increases to compensate the loss and to return to the determined speed.

Conversely, if the speed increases in response to a reduction in the load placed on the motor, the pulse width is reduced by the control device to bring the speed back to the set speed.

Starting from the device for control of the speed of rotation of the motor by the pulse width modulation device, the dental treatment device comprises a device for measuring the torque applied to the file from a measurement 14 of the pulse width.

A measuring process consists in measuring the torque regularly by a calculation based on the PWM control and in comparing it to a torque limit that is set in advance.

At the level of its calculating means 18, the device comprises means that make possible a repeated determination of the torque applied to the file, a repeated comparison of the torque applied to the file at the setting of reference maximum motor torque, a test for detecting the set torque setting spike and an activation of the means for stopping in rotation the file in response to said test.

To do this, the device comprises means 3 for selecting a reference maximum motor torque, means 14 for measuring the torque applied to the file, and means 15 for calculating the maximum torque spike controlling the means 4 for stopping the motor.

Starting from the information of indicating a torque spike, the invention makes it possible to stop the motor in a minimum period of time and by short-circuiting the electromotive force applied to the motor.

To carry out the detection, a digital comparator compares a calculated setting of torque and the pulse width PWM.

When the pulse width exceeds this limit, the torque that is defined by the setting is exceeded, therefore the torque is attained.

The calculating means 18 then provide the order of stopping the motor immediately.

It is conceivable according to the invention, however, to eliminate the ill-timed spikes due to instantaneous control torque variations. To do this, the device can carry out several measurements over a very short time after the spike to verify if the spike is still present and thus to confirm the measurement and to stop the motor.

Another method may consist in limiting the pulse width PWM to the maximum setting which results in dropping the speed or FEM since the pulse width can no longer increase.

To trigger the stop, it will be sufficient to compare the drop in speed or FEM to a fixed setting or a setting that is proportional to the speed to determine the torque spike and therefore the stopping of the motor.

It is also possible to combine the two methods for operational safety, for example in the case of stress impacts, the stopping of the motor is contingent on both the exceeding of the maximum pulse width value and the dropping of the speed of rotation or the electromotive force below a lower limit.

To ensure a quick stopping of the motor, the means 4 for stopping the motor in rotation comprise in particular according to the example means for short-circuiting the electromotive force of the motor.

In a particular embodiment of the process according to the invention, a stage for stopping the motor followed by a stage for slow rotation of the file backwards to release the file while avoiding pushing the dental debris into the apex is provided.

To do this, the device comprises means for timing the stopping of the motor at the calculator 18 and means for control of the motor 16, 17 that are suitable for causing a retraction of the file for a determined period 13 after timing.

An example of a sequence for this function is shown in FIG. 2, whereby this sequence comprises a stage 31 for input of the maximum torque not to be exceeded, a stage 29 for measuring and determining the torque, a stage 30 for comparison and for testing the spike of the set torque, followed, in the case of a maximum torque spike, by a stopping 32 of the motor, a first timing delay 11 and a sequence 12, 13 of timed reverse operation, then a return to normal speed and rotation.

In the case where the measured torque remains less than the maximum torque allowed, the measuring sequence repeats, and the projection of the file continues.

The timing delay 13 during which the file rotates backwards can be fixed so that the retraction of the file is limited to a turn sector immediately after the file stops rotating. This retraction of a turn sector immediately after the stop eliminates the constraint exerted on the file.

Figure 4:
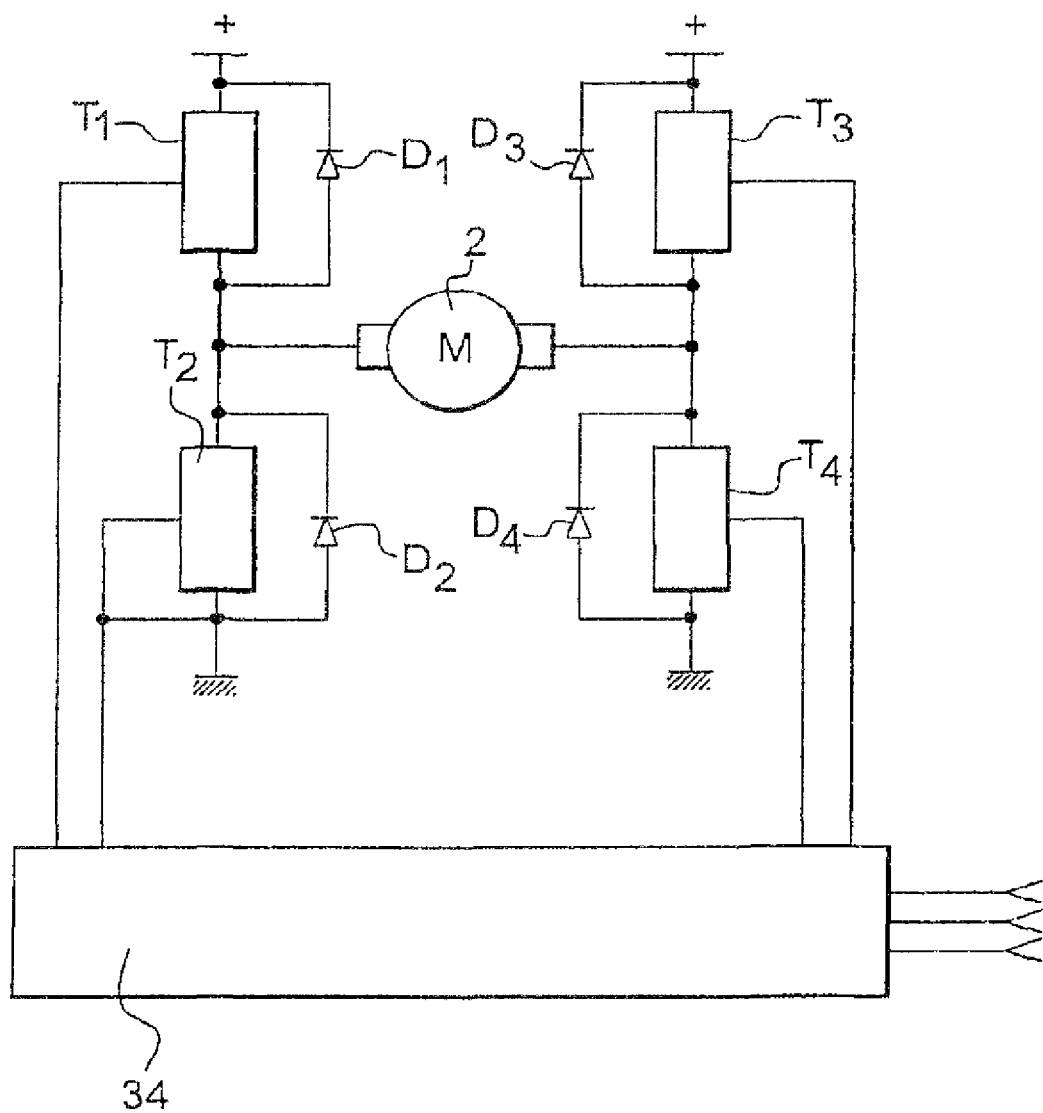
In FIG. 4: A detail of the device describing the system for supplying and quick stopping of the motor.

The different rotation commands of the motor are transmitted to a power control circuit that is described in FIG. 4.

The motor 2 is in particular a motor that is controlled by pulses of a pulse width modulation PWM device. The pulses are relayed by a control logic circuit 34 connected to four H-mounted power transistors T1, T2, T3, and T4 to be able to reverse the voltage in the motor and to obtain two directions of rotation of the file.

The power transistors are preferably VMOS transistors because of their low voltage losses in saturated mode and their ease of control.

D1, D2, D3 and D4 diodes that are parallel to the transistors make it possible to limit the high voltages and are used to short-circuit the motor in quick stopping phase as will be explained below.

The device according to the invention comprises means 4 for stopping the motor. These means are in particular means for short-circuiting the electromotive force of the motor carried out by a particular configuration for controlling transistors.

In normal operation, the control logic is configured to make two transistors in diagonal conductive. For example, if the positive rotation direction corresponds to T1 and T4 open, the transistors T2, T3 of the other diagonal are locked for this direction of rotation.

Leaving a normal rotation, when the stop is requested, the control pulses are stopped and T1 becomes non-conductive. To ensure a quick stop, T4 is kept conductive, and the FEM of the motor is short-circuited by conductive T4 and the backward diode of T2 that closes the circuit in the motor, which stops very quickly.

It is possible to improve upon the principle by an additional command and by a series of ports and to make T4 and T2 conductive during the stopping phase, thus totally short-circuiting the FEM of the motor that stops instantaneously.

According to the example of FIG. 4, T3 receives pulses from the generator, T2 is conductive, T1 and T4 are not conductive, for a brief instant, the motor rotates backwards, which makes it possible for the file to rotate by one turn sector before stopping the PWM generator by T3 that becomes non-conductive, which controls the stopping of the motor.

When the device detects the conditions of the motor stopping on excess torque or on slowed speed, it alerts the practitioner via alert means 9, 10 that the device has stopped and that it will go into reverse because the practitioner should at this time draw the file for a given timing delay, for example 1 second.

Then, the device rotates the file slowly backwards, either at slow speed, for example 100 rpm, or advantageously by gradually increasing the speed in reverse going from zero speed to slow speed in several seconds, for example in 1 to 2 seconds to release the file without pushing the debris into the apical region up to an acceptable level, for example 2 mm, and to leave again in the normal direction and at normal speed before returning gently to the apex.

The measurement of torque and the process according to the invention therefore make it possible to gain time when the torque and/or the position have effectively exceeded the limit fixed by the setting or settings and make it possible to act before the file is broken and to avoid exceeding the apex when the inertia of the mechanics drives the motor and the file farther than anticipated.

The invention is not limited to the example shown and in particular can be applied to portable and/or stationary devices, provided with means for measuring the advance of the file that are different from measuring means with electrodes.

The invention claimed is:

1. A rotary-file dental treatment device (1) that is driven by a motor (2), comprising:
   a means (3, 18) for fixing a root canal position setting relative to the apex of a tooth,
   a means (4) for stopping the motor based on the position of the file (1) relative to said position setting,
   a first means (5) for measuring, and a first means (6) for calculating the remaining root canal length (L) between the file and the position setting, wherein the first means for calculating comprises second means (7, 7a, 7b) for calculating at least one value (D) derived from the remaining root canal length and third means (8, 8a, 8b, 8c, 8d, 8e) for calculating, suitable for combining the derived value and the remaining root canal length, whereby the combination of the derived value and the root canal length by the first, second and third means for calculating (6, 7, 8, 8a, 8b, 8c, 8d, 8e) control the means for stopping the motor so as to stop the rotation of the file in anticipation of the position setting.

2. The rotary-file dental treatment device according to claim 1, wherein said derived value (D) comprises the first derivative of the remaining root canal length.

3. The rotary-file dental treatment device according to claim 1, wherein said derived value (D) comprises the second derivative of the remaining root canal length.

4. The rotary-file dental treatment device according to claim 1, wherein the third means for calculating (8, 8a, 8d, 8e) calculates the derived value (D) by a calculated adjustment coefficient.

5. The rotary-file dental treatment device according to claim 1, further comprising:
at least one of a visual (10) or audio (9) output device for alerting an operator that are triggered upon an activation of the means for stopping the motor.

6. The rotary-file dental treatment device according to claim 1, further comprising:
a timing delay for stopping of the motor, and
a means (12) for controlling the motor in slow reverse for a determined period (13) after timing.

7. The rotary-file dental treatment device according to claim 1, further comprising:
a means (3) for selecting a reference maximum motor torque,
a means (14) for measuring the torque applied to the file, and
a microprocessor (18) programmed to calculate the maximum torque spike controlling the means (4) for stopping the motor.

8. The rotary file dental treatment device according to claim 7,
wherein the programmed microprocessor performs a repeated determination of the torque applied to the file by a measurement (29), a test (30) for detecting the spike of a torque setting (31) and an activation (32) of the means for stopping the motor in rotation in response to said test.

9. The rotary-file dental treatment device according to claim 1, further comprising:
a controller (16, 17) controlling the motor that is suitable for causing a retraction of the file from a turn sector immediately after stopping the file in rotation.

10. The rotary-file dental treatment device according to claim 1, wherein the motor is supplied by a pulse width modulation device, the rotary-file dental treatment device comprises a device for controlling the rotation speed of the motor by use of the pulse width modulation device and a device for measuring the torque applied to the file starting from a measurement of the pulse width.

11. The rotary-file dental treatment device according to claim 1, wherein the means (4) for stopping the motor in rotation comprise means for short-circuiting the electromotive force of the motor.

12. A process for controlling the rotation of a file of the dental treatment device according to claim 1, comprising:
repeatedly determining a distance from the file to a root canal position setting relative to the apex of a tooth by measurement (26), the repeatedly determining performed by calculation (27) of a value derived from said distance and a repeated calculation (28) of an early stopping position of the rotation of the file based on the distance from the file to said position setting that is weighted by a coefficient based on said value derived from said distance.

13. The process for controlling the rotation of a file of the dental treatment device according to claim 12, further comprising:
a stage (33) for anticipation of an activation of means for stopping the motor in rotation based on the value of said value derived from said distance.

14. The process for controlling the rotation of a file of the dental treatment device according to claim 12 further comprising:
a slow rotation stage of the file in reverse (12) after a time delay (11) following an activation (32) of the means for stopping the motor.

15. The process for controlling the rotation of a file of the dental treatment device according to claim 12, further comprising:
a stage of gradually increasing the speed of the file (12) in reverse after a time delay (11) following an activation (32) of the means for stopping the motor.

* * * * *